United States Patent [19]
Baudino

[11] Patent Number: 6,110,155
[45] Date of Patent: Aug. 29, 2000

[54] ANTI-INFLAMMATORY-AGENT-LOADED CATHETER AND METHOD FOR PREVENTING TISSUE FIBROSIS

[75] Inventor: Michael D. Baudino, Coon Rapids, Minn.

[73] Assignee: Medtronic, Inc., Minneapolis, Minn.

[*] Notice: This patent issued on a continued prosecution application filed under 37 CFR 1.53(d), and is subject to the twenty year patent term provisions of 35 U.S.C. 154(a)(2).

[21] Appl. No.: 08/643,145

[22] Filed: Apr. 30, 1996

[51] Int. Cl.7 ....................................... A61M 5/32
[52] U.S. Cl. ................. 604/265; 604/264; 604/523; 604/890.1; 604/891.1; 604/93.01
[58] Field of Search ................. 604/265, 53, 93, 604/48, 19–22, 264, 891.1, 892.1, 890.1, 508, 93.01, 523

[56] References Cited

U.S. PATENT DOCUMENTS

| | | | |
|---|---|---|---|
| 4,010,758 | 3/1977 | Rockland et al. | 128/418 |
| 4,506,680 | 3/1985 | Stokes | 128/786 |
| 4,577,642 | 3/1986 | Stokes | 128/784 |
| 4,601,724 | 7/1986 | Hoover et al. | 623/66 |
| 4,606,118 | 8/1986 | Cannon et al. | 29/825 |
| 4,711,251 | 12/1987 | Stokes | 128/784 |
| 4,951,687 | 8/1990 | Ufford et al. | 128/786 |
| 5,002,067 | 3/1991 | Berthelsen et al. | 128/786 |
| 5,041,107 | 8/1991 | Heil, Jr. | 604/891.1 |
| 5,092,332 | 3/1992 | Lee et al. | 128/642 |
| 5,265,608 | 11/1993 | Lee et al. | 128/642 |
| 5,282,844 | 2/1994 | Stokes et al. | 607/120 |
| 5,345,933 | 9/1994 | Peterson et al. | 128/639 |
| 5,451,215 | 9/1995 | Wolter | 604/265 |
| 5,458,632 | 10/1995 | Preidel et al. | 607/121 |
| 5,468,562 | 11/1995 | Farivar et al. | 428/457 |
| 5,512,055 | 4/1996 | Domb et al. | 604/265 |
| 5,609,629 | 3/1997 | Fearnot et al. | 623/1 |
| 5,628,730 | 5/1997 | Shapland et al. | 604/21 |
| 5,717,030 | 2/1998 | Dunn et al. | 523/111 |
| 5,762,638 | 6/1998 | Shikani et al. | 604/265 |
| 5,788,979 | 8/1998 | Alt et al. | 424/426 |
| 5,824,048 | 10/1998 | Tuch | 623/1 |
| 5,879,697 | 3/1999 | Ding et al. | 424/422 |

*Primary Examiner*—Corrine McDermott
*Assistant Examiner*—Cris L. Rodriguez
*Attorney, Agent, or Firm*—Curtis D. Kinghorn; Harold R. Patton

[57] ABSTRACT

At least a portion of a catheter which is intended to be in contact with bodily tissue for more than a nominal period of time is loaded with an anti-inflammatory agent such as dexamethasone sodium phosphate. The direct loading or compounding of the catheter with the agent resists inflammation and encapsulation of the catheter as a result of the tissue's natural foreign-body response. The anti-inflammatory agent can be provided as a coating or bonded on the outside of the catheter or can be integrally compounded into the body of the catheter.

5 Claims, 2 Drawing Sheets

ANTI-INFLAMMATORY-AGENT-LOADED
CATHETER AND METHOD FOR
PREVENTING TISSUE FIBROSIS

BACKGROUND OF THE INVENTION

1. Field of the Invention

This invention relates to catheters for the conduction of fluids to and from internal bodily organs, and more particularly, to a catheter which is loaded or impregnated with an anti-inflammatory agent to obviate or abate the human foreign-body response to the implanted catheter.

2. Description of the Related Art

Catheters have long found innumerable applications in a wide variety of medical procedures, including both therapeutic and diagnostic procedures. Catheters are eminently useful, for example, as passageways for delivery of fluids to the patient and removal of fluids from the patient. They are thus routinely employed to conduct fluids containing medicaments from a source thereof directly to the tissue of an internal organ. Such catheters may be placed in the parenchyma of an organ such as the brain or pancreas for direct delivery of medicaments to the parenchyma, usually by way of a bore formed in the tissue of the parenchyma by incision, perforation or puncture.

The human body spontaneously rejects or encapsulates a foreign body which has been introduced into the body or a specific bodily organ. Such phenomena in connection with implants are described with particularity in U.S. Pat. No. 5,219,361, issued Jun. 15, 1993 to A. F. von Recum et al. In some cases, encapsulation will impede or halt infusion through blockage of the catheter. In essence, the body's own natural defense systems frustrate the potentially beneficial procedure of directly removing or supplying fluid to the tissue.

SUMMARY OF THE INVENTION

The anti-inflammatory agent infused catheter of the invention overcomes problems of the prior art by acting as a continuous and immediately available source of anti-inflammatory agent, thereby preventing or minimizing the natural responses of the tissue to a foreign body.

More particularly, the invention provides an infusion catheter having a distal end to be positioned adjacent to bodily tissue for the conduction of fluid thereto or therefrom, the distal end carrying an anti-inflammatory agent to be leached therefrom when the distal end is in contact with bodily tissue and fluid to combat inflammation of the tissue and encapsulation of the catheter thereby.

The invention also provides a method of abating fibrosis of bodily tissue surrounding a catheter, the method comprising the steps of providing an infusion catheter; compounding an anti-inflammatory agent with a polymeric material and incorporating the compound with the catheter in a manner whereby the anti-inflammatory agent will be leached from the polymeric material when the catheter is in fluid contact with bodily tissue; inserting the catheter into a body with at least a portion of the catheter disposed adjacent to bodily tissue; and conducting fluid through the catheter to or from the tissue; whereby to combat fibrosis of the body tissue adjacent to the catheter by the introduction of the anti-inflammatory agent thereto.

The invention further provides a method of forming an anti-inflammatory-agent-loaded catheter comprising the steps of providing an infusion catheter; providing a composite formed of a polymeric material and an anti-inflammatory agent; and utilizing the composite in at least a portion of the exterior surface of the catheter; whereby the anti-inflammatory agent will be leached from the coating when the coated portion is in contact with bodily fluid.

Finally, the invention provides a method of forming an anti-inflammatory agent loaded catheter comprising the steps of providing an infusion catheter; preparing at least a portion of the surface of the catheter in a manner to provide a first electrical molecular charge prevalent on the surface; providing a compound having an anti-inflammatory agent and a second electrical molecular charge which is attracted to the first electrical molecular charge; and applying a coating to at least a portion of the surface of the catheter by covalently bonding the compound to the surface; whereby the anti-inflammatory agent will be leached from the coating when the catheter is in contact with bodily fluid.

In each case, the anti-inflammatory agent preferably comprises dexamethasone sodium phosphate.

These and other objects, features and advantages of the invention will be apparent from the ensuing description in conjunction with the accompanying drawings. Throughout the disclosure, like elements, wherever mentioned or referred to, are referenced with like reference numbers.

Figure 1:
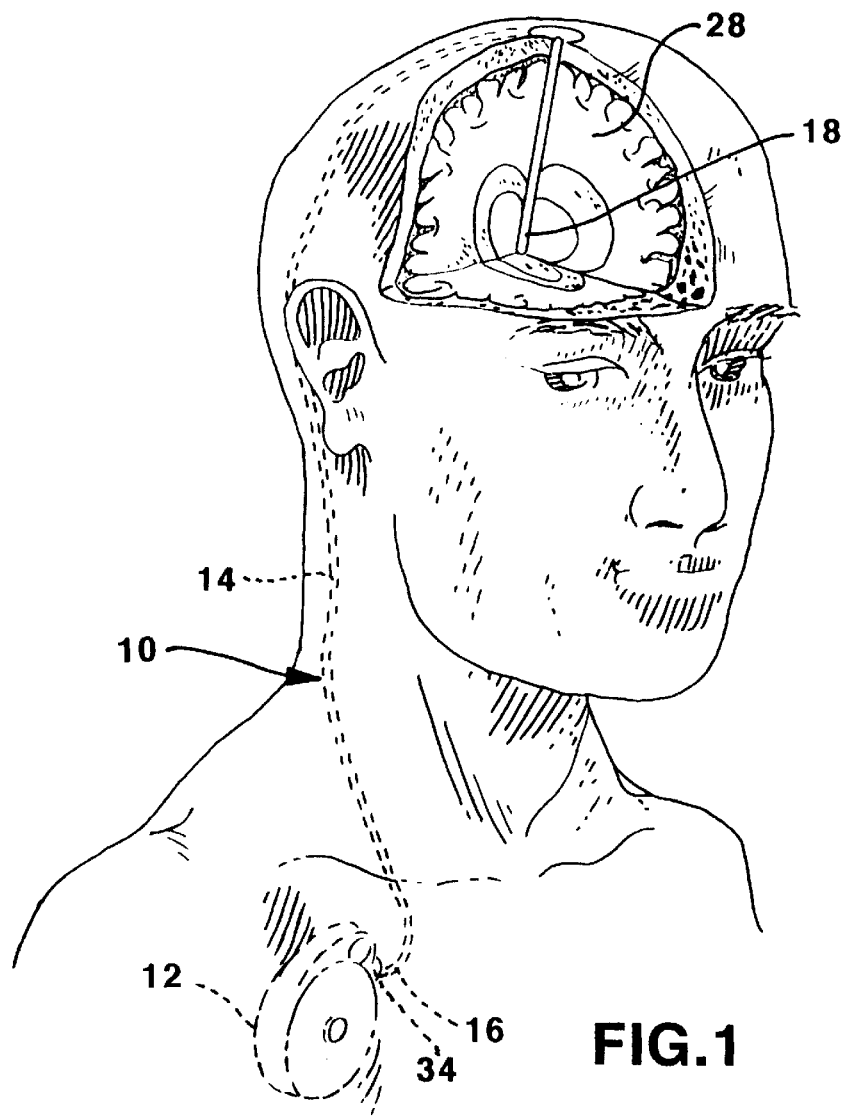
FIG. 1 is a schematic representation of a fluid delivery system surgically implanted in a patient and including an anti-inflammatory-agent-loaded catheter according to the invention.

DETAILED DESCRIPTION OF THE
PREFERRED EMBODIMENTS

Referring to the drawings, an infusion-catheter fluid-delivery system 10 for medicaments comprises a combined fluid pump and reservoir 12 and an infusion catheter 14. A proximal end 16 of the catheter 14 is secured to the pump reservoir 12, whereas an opposite, distal end 18 is adapted to be positioned immediately adjacent to the tissue intended to receive the medicament. A lumen 20 extends from the proximal end 16 to the distal end 18 of the catheter to conduct the flow of fluid therebetween.

The pump-reservoir 12 comprises any suitable means for conveying fluid to or from a suitable source by way of catheter 14. The pump-reservoir is preferably implanted in the patient and includes a self-contained reservoir for storing medicament, a pump (not shown) for drawing the medicament fluid from the reservoir and advancing it by way of infusion catheter 14 to the tissue to be treated, and a suitable power source, such as a battery, for energizing the pump. An example of a suitable pump-reservoir is the SynchroMed™ programmable pump, available from Medtronic, Inc. of Minneapolis, Minn. The pump-reservoir 12 is surgically implanted in the patient and programmed to deliver prescribed amounts of medicament continuously, on demand, or at regularly scheduled intervals. The fluid delivery system 10 can be modified by providing an external source of fluid, rather than the internal pump or can be used with external means, such as a pump, for withdrawing fluid from the body through the catheter 14.

In the preferred embodiments, proximal end 16 of the catheter is secured to an outlet port 34 of the pump-reservoir 12. As seen in FIG. 1, the pump-reservoir 12 is surgically implanted in subcutaneous tissue, and the infusion catheter 14 extends internally to the parenchyma of the brain tissue 28 so that medicament is conducted directly from the pump-reservoir to the brain tissue. This type of delivery system is ideal for medications that are not readily or efficiently absorbed and delivered where needed by way of the digestive and circulatory systems. For example, nerve growth factors cannot, at present, be directed to the brain tissue effectively except by direct application using a catheter.

Figure 2:
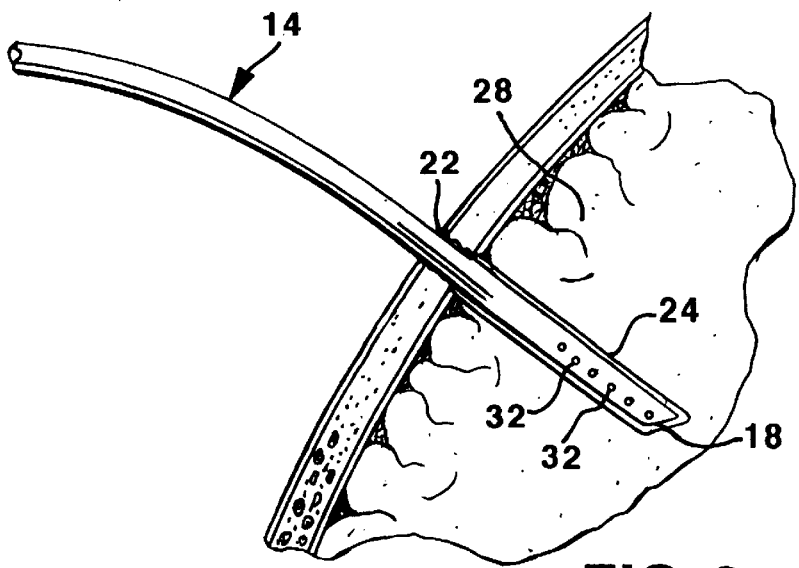
FIG. 2 is an enlarged, partial sectional view of a catheter according to the invention inserted in a patient's brain for directly infusing medicaments into the parenchyma thereof.

FIG. 2 more specifically shows means for conducting fluid to or from the human body employing the catheter according to the invention. Here, the distal end 18 of the catheter 14 is received in an opening 22 formed in a patient's skull and in a bore 24 formed in his brain tissue 28. In this embodiment, multiple fluid apertures 32 are provided in the catheter adjacent to the distal end 18, whereby fluid such as a suitable medicament can be conducted directly to the bore 24 in the brain tissue. Alternatively, a source of negative pressure can be applied to the proximal end 16 of the catheter 14 to withdraw fluid from the area adjacent to the implanted, distal end 18 of the catheter 14.

As noted above, a problem inherent in the implantation of a foreign body in human tissue is the tissue inflammatory encapsulation of the catheter known as the foreign-body response. The present invention overcomes this problem by loading or compounding at least a portion of the implanted catheter with an anti-inflammatory agent such as dexamethasone sodium phosphate. While the preferred embodiment employs dexamethasone sodium phosphate, it is understood that any agent which combats the foreign-body response can be substituted for or used in addition to dexamethasone sodium phosphate.

Figure 3:
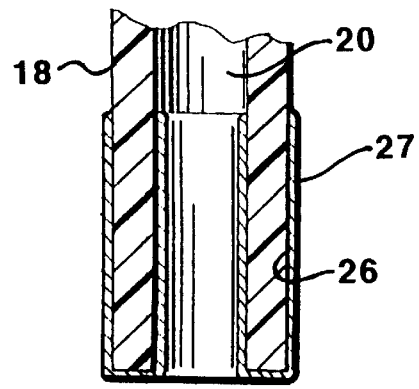
FIG. 3 is a greatly enlarged, partial, longitudinal sectional view of the distal end of the first embodiment of the loaded catheter according to the invention.

In the embodiment depicted in FIG. 3, the surface 26 of the distal end 18 of the catheter is provided with a coating 27 of dexamethasone sodium phosphate loaded material. For example, a silicon-based catheter can be dipped into a silicon adhesive in which dexamethasone sodium phosphate has been placed into solution. The compound liquid coats the surface 26 of the catheter and, as it solidifies, encapsulates at least a portion of the distal end in the polymer/anti-inflammatory agent compound. By the use of this structure, dexamethasone sodium phosphate is leached from the catheter when the catheter is in contact with body fluid and acts to combat inflammation and encapsulation. An alternative to dipping the distal end of the catheter is to spray-coat the distal end of the catheter with a vaporized, compounded solution.

Figure 4:
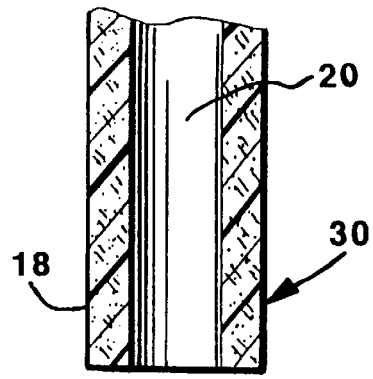
FIG. 4 is a view similar to that of FIG. 3, but of a second embodiment of the catheter according to the invention.

FIG. 4 depicts an alternative embodiment of the catheter according to the invention. In this embodiment, the anti-inflammatory agent, again preferably dexamethasone sodium phosphate, is provided throughout the body of the catheter by mixing and compounding the anti-inflammatory agent directly into the catheter polymer melt before forming the catheter. For example, dexamethasone sodium phosphate can be compounded into materials such as silicone rubber or urethane. The compounded material is then processed conventionally as by extrusion, transfer molding or casting, for example, to form a tubular configuration. The catheter 30 resulting from this process benefits by having an anti-inflammatory agent dispersed throughout the entire catheter body. The anti-inflammatory agent will slowly leach or diffuse into the body fluid from the catheter, thereby preventing or resisting inflammation and encapsulation in and around the catheter 30.

Figure 5:
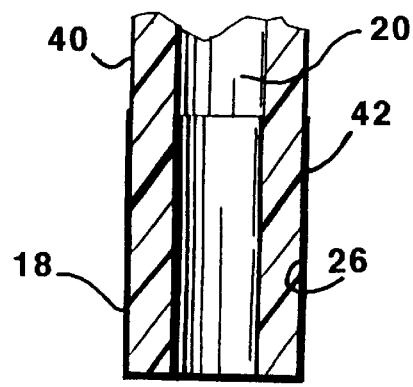
FIG. 5 is a view similar to that of FIG. 3, but of a third embodiment of the catheter according to the invention.

Still another embodiment of the catheter according to the invention is seen in FIG. 5. In this embodiment, a thin layer 42 of an anti-inflammatory agent such as dexamethasone sodium phosphate has been covalently bonded to the exterior surface 26 of the catheter 14. The surface is prepared to molecularly receive dexamethasone sodium phosphate molecules. A binding agent may be needed between the anti-inflammatory agent molecules and the polymer molecules on the surface 26. With this structure, the dexamethasone sodium phosphate molecules are present on the exterior surface of the catheter and can be leached away to combat encapsulation.

The invention has been shown and described primarily with reference to an infusion-catheter fluid-delivery system 10 for medicaments comprising a combined fluid pump and reservoir 12 and an infusion catheter 14. It is also within the scope of the invention to use a catheter access port or additional forms of implantable pump systems in place of the combined fluid pump and reservoir 12 disclosed. An example of a suitable catheter access port is disclosed in U.S. Pat. No. 5,137,529 issued to David A. Watson, Mark J. Licata, Alfons Heindl and Edward C. Leicht on Aug. 11, 1992 entitled "Injection Port" and assigned to Medtronic-PS Medical, the disclosure of which is incorporated herein by reference in its entirety. Examples of additional implantable pump systems are disclosed in U.S. Pat. No. 4,588,394 issued to Rudolf R. Schultz, Gary P. East and Alfons Heindle on May 13, 1986 entitled "Infusion Reservoir and Pump System", U.S. Pat. No. 4,681,560 issued to Rudolf R. Schultz, Gary P. East and Alfons Heindle on Jul. 21, 1987 entitled "Subcutaneous Infusion Reservoir and Pump System", U.S. Pat. No. 4,761,158 issued to Rudolf R. Schultz, Gary P. East and Alfons Heindle on Aug. 2, 1988 entitled "Subcutaneous Infusion Reservoir and Pump System", U.S. Pat. No. 4,816,016 issued to Rudolf R. Schultz, Gary P. East and Alfons Heindle on Mar. 28, 1989 entitled "Subcutaneous Infusion Reservoir and Pump System", U.S. Pat. No. 4,867,740 issued to Gary P. East on Sep. 19, 1989 entitled "Multiple-Membrane Flow Control Valve and Implantable Shunt System", U.S. Pat. No. 5,085,644 issued to David A. Watson and Mark J. Licata on Feb. 4, 1992 entitled "Sterilizable Medication Infusion Device with Dose Recharge Restriction" and U.S. Pat. No. 5,152,753 issued to Stephen W. Laguette, Gary P. East, David A. Watson and Thomas J. Carlisle on Oct. 6, 1992 entitled "Medication Infusion Device with Dose Recharge Restriction", all of which are assigned to Medtronic-PS Medical, the disclosures of which are incorporated herein by reference in their entirety.

It will be understood from the foregoing description that the anti-inflammatory-agent-loaded catheter according to the invention provides a direct and continuous supply of an anti-inflammatory agent directly to the adjacent fluid and tissue to combat the natural foreign-body response. By the use of the structures disclosed herein, fluid can be directly infused into or withdrawn from bodily tissue without encapsulation of the catheter.

While the invention has been particularly described in connection with certain specific embodiments thereof, it is to be understood that this is by way of illustration and not of limitation, and the scope of the appended claims should be construed as broadly as the prior art will permit.

What is claimed is:

1. An infusion catheter having a body with an exterior surface and a distal end to be positioned adjacent to bodily tissue for the conduction of fluid thereto or therefrom, the distal end carrying dexamethasone sodium phosphate covalently bonded to the exterior surface at least at the distal end, the dexamethasone sodium phosphate forming the ultimate exterior surface of the catheter where the dexamethasone sodium phosphate is bonded to the body, the dexamethasone sodium phosphate to be leached therefrom when the distal end is in contact with bodily tissue and fluid to combat inflammation of the tissue and encapsulation of the catheter thereby.

2. An infusion catheter according to claim 1, wherein the body of the catheter is formed of a polymeric material, the anti-inflammatory agent being dispersed throughout the polymeric material.

3. An infusion catheter according to claim 2, wherein the polymeric material is selected from the group consisting of urethane and silicone.

4. An infusion catheter having a body with an exterior surface and a distal end to be positioned adjacent to bodily tissue for the conduction of fluid thereto or therefrom, the body and the exterior surface of the catheter being made of a polymeric material, the distal end having dexamethasone sodium phosphate covalently bonded directly to the polymeric material of the exterior surface at least at the distal end, the dexamethasone sodium phosphate forming the ultimate exterior surface of the catheter where the dexamethasone sodium phosphate is bonded to the body, the dexamethasone sodium phosphate to be leached into bodily tissue and fluid when the distal end is in contact with bodily tissue and fluid to combat inflammation of the tissue and encapsulation of the catheter thereby.

5. An infusion catheter according to claim 4, wherein the polymeric material is selected from the group consisting of urethane and silicone.

* * * * *